（12） United States Patent
Koh

(10) Patent No.: US 9,271,687 B2
(45) Date of Patent: Mar. 1, 2016

(54) METHOD AND APPARATUS FOR ADJUSTING AN X-RAY EMISSION RANGE

(75) Inventor: Byoung-hoon Koh, Gyeonggi-do (KR)

(73) Assignee: Samsung Electronics Co., Ltd., Yeongtong-gu, Suwon-si, Gyeonggi-do (KR)

( * ) Notice: Subject to any disclaimer, the term of this patent is extended or adjusted under 35 U.S.C. 154(b) by 682 days.

(21) Appl. No.: 13/551,719

(22) Filed: Jul. 18, 2012

(65) Prior Publication Data

US 2013/0163721 A1    Jun. 27, 2013

(30) Foreign Application Priority Data

Dec. 27, 2011 (KR) .......................... 10-2011-0143925

(51) Int. Cl.
*A61B 6/00* (2006.01)
*A61B 6/06* (2006.01)

(52) U.S. Cl.
CPC . *A61B 6/469* (2013.01); *A61B 6/06* (2013.01); *A61B 6/548* (2013.01)

(58) Field of Classification Search
USPC .............................................. 378/62, 65, 98.7
See application file for complete search history.

(56) References Cited

U.S. PATENT DOCUMENTS

| 6,106,152 | A | 8/2000 | Thunberg | |
|---|---|---|---|---|
| 7,336,768 | B2 | 2/2008 | Ogawa | |
| 8,605,861 | B2 * | 12/2013 | Sipiorski | ...................... 378/98.7 |
| 2006/0241370 | A1 | 10/2006 | Kramp et al. | |
| 2007/0025500 | A1 | 2/2007 | Horiuchi et al. | |
| 2007/0071171 | A1 * | 3/2007 | Hayashida et al. | .............. 378/98 |
| 2009/0014629 | A1 * | 1/2009 | Tsuchiya | ................... 250/208.1 |
| 2010/0027752 | A1 * | 2/2010 | Matsumoto | .................... 378/115 |
| 2010/0128955 | A1 | 5/2010 | Walimbe et al. | |
| 2010/0310049 | A1 | 12/2010 | Sipiorski | |
| 2011/0293164 | A1 * | 12/2011 | Sato et al. | ...................... 382/132 |
| 2012/0059239 | A1 * | 3/2012 | Yamaguchi | ................... 600/407 |

FOREIGN PATENT DOCUMENTS

| CN | 1315434 | C | 5/2007 |
|---|---|---|---|
| EP | 2394579 | A1 | 12/2011 |
| JP | 2005-245797 | A | 9/2005 |
| JP | 2006-255241 | A | 9/2006 |
| JP | 2008-212550 | A | 9/2008 |
| JP | 2009-136425 | A | 6/2009 |
| KR | 10-2008-0071724 | A | 8/2008 |
| KR | 10-2009-0078506 | A | 7/2009 |
| KR | 10-1042046 | B1 | 6/2011 |
| WO | 98/27867 | A1 | 7/1998 |
| WO | 2006-038165 | A1 | 4/2006 |

* cited by examiner

*Primary Examiner* — Kiet T Nguyen
(74) *Attorney, Agent, or Firm* — Cha & Reiter, LLC

(57) ABSTRACT

A method of adjusting an X-ray emission range includes: displaying an image obtained by capturing X-rays which pass through a subject; receiving a user input with respect to the captured image; and controlling a collimator according to the received user input, to adjust the X-ray emission range according to a size and position of the collimator.

37 Claims, 6 Drawing Sheets

METHOD AND APPARATUS FOR ADJUSTING AN X-RAY EMISSION RANGE

CLAIM OF PRIORITY

This application claims, pursuant to 35 U.S.C. §119(a), priority to and the benefit of the earlier filing date of Korean Patent Application No. 10-2011-0143925, filed on Dec. 27, 2011, in the Korean Intellectual Property Office, the disclosure of which is incorporated herein in its entirety by reference.

BACKGROUND OF THE INVENTION

1. Field of the Invention

The present invention relates to a method and apparatus for adjusting an X-ray emission range, and more particularly, to a method and apparatus for adjusting an X-ray emission range by adjusting a size and position of a collimator.

2. Description of the Related Art

In the field of radiation transmission capturing apparatuses for the medical industry, capturing apparatuses using X-rays have been developed and used. In such capturing apparatuses using X-rays, when X-rays emitted from an X-ray source pass through an object, such as a subject including a patient, a scintillator included in such capturing apparatuses converts the emitted X-rays to a visible ray depending on the density of the subject, and the visible ray is converted to an electric signal by a photodiode included in the capturing apparatuses. Accordingly, the capturing apparatuses using X-rays display a digital image of the subject through which the X-rays have passed by using the electric signal.

In general, a collimator is a device for changing diverging light emitted from a point light source to parallel light rays. Changing the paths of light rays to be parallel is required for precise measurement in spectroscopy, geometry, and physical optics. In particular, a collimator used in radiology is an absorbing device for adjusting a beam radius size and a beam divergence angle of an X-ray, a gamma ray, or nuclear particles according to a specific purpose. That is, the collimator is generally used to adjust an X-ray or a gamma ray so that a beam radius size of the X-ray or the gamma ray is constant when incident on a subject.

SUMMARY OF THE INVENTION

The present invention provides a method and apparatus for adjusting an X-ray emission range.

According to an aspect of the present invention, there is provided a method of adjusting an X-ray emission range, the method including: displaying an image obtained by capturing X-rays which pass through an object; receiving a user input with respect to the captured image; and controlling a collimator according to the received user input, wherein an X-ray emission range is adjusted according to a size and position of the collimator.

The method may further include: selecting a predetermined area in the captured image; and providing a magnified image of the predetermined area.

The method may further include detecting an emitted X-ray, and the detecting of the emitted X-ray may include detecting the intensity of the X-ray with respect to an image captured using the X-ray emitted through the collimator.

According to another aspect of the present invention, there is provided a method of adjusting an X-ray emission range, the method including: acquiring image information from an image obtained by capturing X-rays which pass through an object; selecting a predetermined area in the captured image based on the acquired image information; and controlling a collimator based on the selected predetermined area, wherein the X-ray emission range is adjusted according to a size and position of the collimator.

The method may further include detecting an emitted X-ray, and the detecting of the emitted X-ray may include detecting the intensity of the X-ray with respect to an image captured using the X-ray emitted through the collimator.

According to another aspect of the present invention, there is provided an apparatus for adjusting an X-ray emission range, the apparatus including: a display unit for displaying an image obtained by capturing X-rays which pass through an object; a user input unit for receiving a user input with respect to the displayed image; and a controller for controlling a collimator according to the received user input, wherein the X-ray emission range is adjusted according to a size and position of the collimator.

The apparatus may further include: an area selector for selecting a predetermined area in the captured image based on the user input.

According to another aspect of the present invention, there is provided an apparatus for adjusting an X-ray emission range, the apparatus including: an image information acquisition unit for acquiring image information from an image obtained by capturing X-rays which pass through an object; an area selector for selecting a predetermined area in the captured image based on the acquired image information; and a controller for controlling a collimator based on the selected predetermined area, wherein the X-ray emission range is adjusted according to a size and position of the collimator.

The apparatus may further include a detector for detecting an emitted X-ray, wherein the detector detects the intensity of the X-ray with respect to an image captured using the X-ray emitted through the collimator.

According to another aspect of the present invention, there is provided a computer-readable recording medium storing a computer-readable program for executing the method.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1:
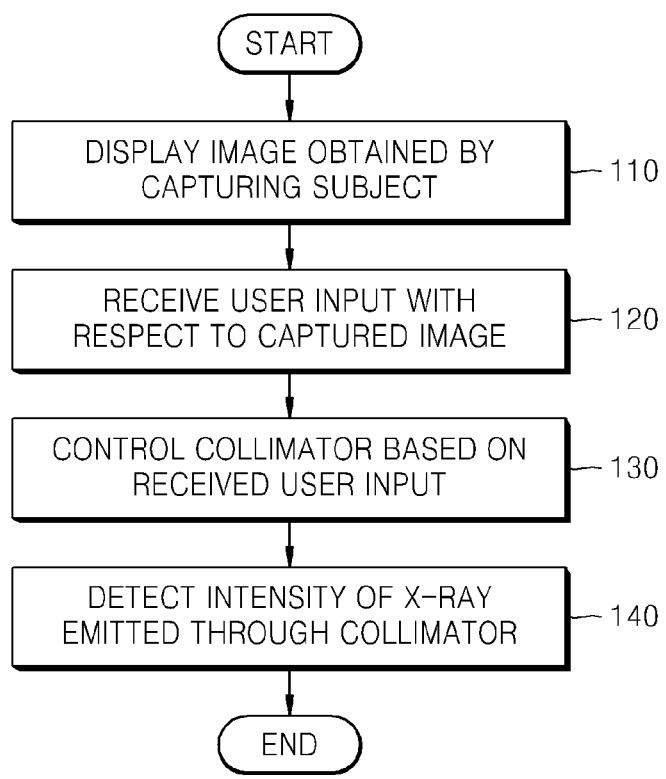
FIG. 1 is a flowchart illustrating a method of adjusting an X-ray emission range, according to an exemplary embodiment of the present invention.

The terms used in the specification will be schematically described, and then, the present invention will be described in detail.

Although general terms as currently widely used as possible are selected as the terms used in describing the present invention while taking functions in the present invention into account, they may vary according to an intention and practice of those of ordinary skill in the art, judicial precedents, or the appearance of new technology. In addition, in specific cases, terms intentionally selected by the applicant may be used, and in this case, the meaning of the terms will be disclosed in corresponding description of the invention. Accordingly, the terms used in the present invention should be defined not by simple names of the terms but by the meaning of the terms and the overall content the present invention. Therefore, the terms should be understood on the basis of the disclosure throughout the specification. The principles and features of this invention may be employed in varied and numerous embodiments without departing from the scope of the invention.

In the specification, when a certain part "includes" a certain component, this indicates that the part may further include another component instead of excluding another component unless there is no different disclosure. In addition, the term, such as "unit" or "module," disclosed in the specification indicates a unit for processing at least one function or operation, and this may be implemented by hardware, software, or a combination of them.

Hereinafter, preferred embodiments of the present invention will be described in detail with reference to the accompanying drawings so that those of ordinary skill in the art may easily realize the present invention. However, the present invention may be embodied in many different forms and should not be construed as being limited to the exemplary embodiments set forth herein. In the following description, a detailed explanation of known related functions and constructions may be omitted to avoid unnecessarily obscuring the subject matter of the present invention.

Furthermore, although the drawings represent exemplary embodiments of the invention, the drawings are not necessarily to scale and certain features may be exaggerated or omitted in order to more clearly illustrate and explain the present invention.

In the drawings, parts irrelevant to the description are omitted to clearly describe the present invention, and like reference numerals denote like elements throughout the specification.

Although radiation transmission capturing apparatuses are occasionally used in the medical industry, exposure of an object, such as a subject including human patients, to a large amount of radiation may cause a change in a state, a form, etc. of the subject, such as illness due to radiation exposure. In addition, when observation of a portion of a subject is required, if an image of the portion is used instead of an entire image of the subject, the amount of image data to be processed is reduced, thereby enhancing a processing speed of image data.

Figure 3:
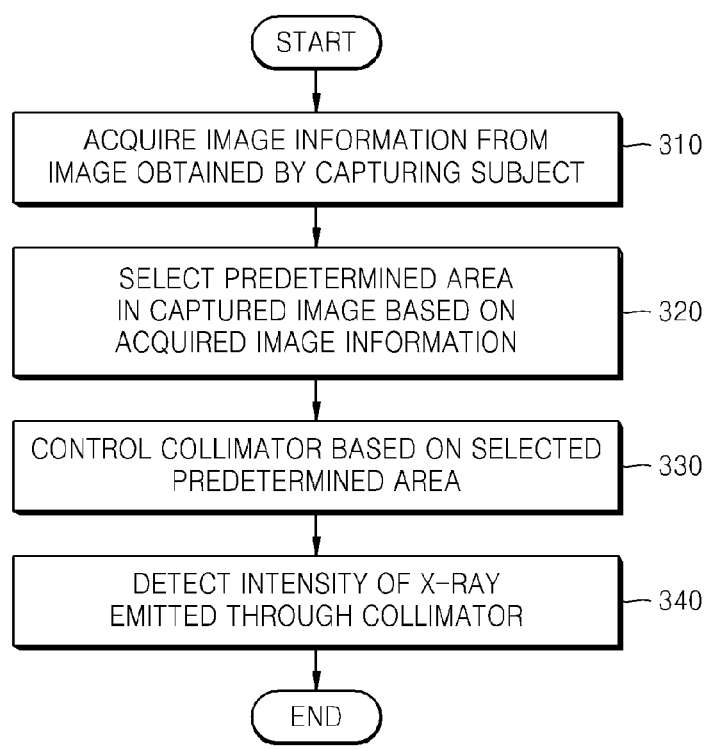
FIG. 3 is a flowchart illustrating a method of adjusting an X-ray emission range, according to an alternative exemplary embodiment of the present invention.
Figure 4A:
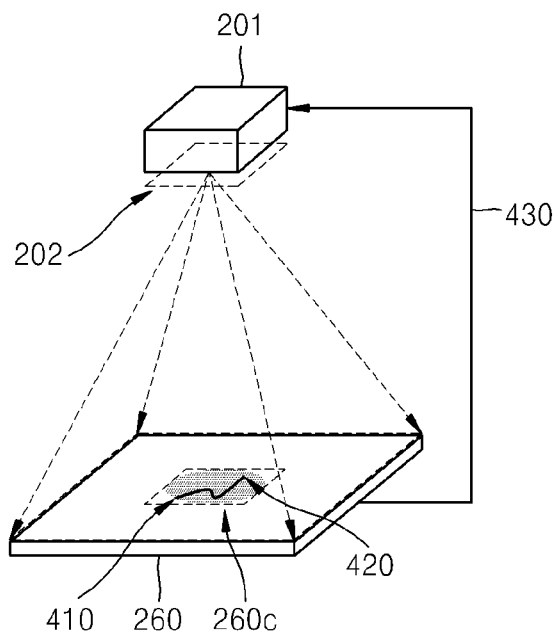
FIGS. 4A-4B illustrate controlling of a position or aperture size of the collimator, according to the alternative exemplary embodiment of the present invention of FIG. 3.
Figure 4B:
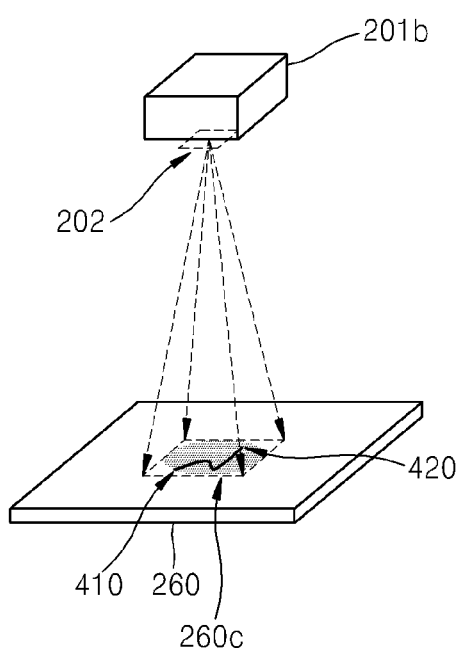
Figure 5:
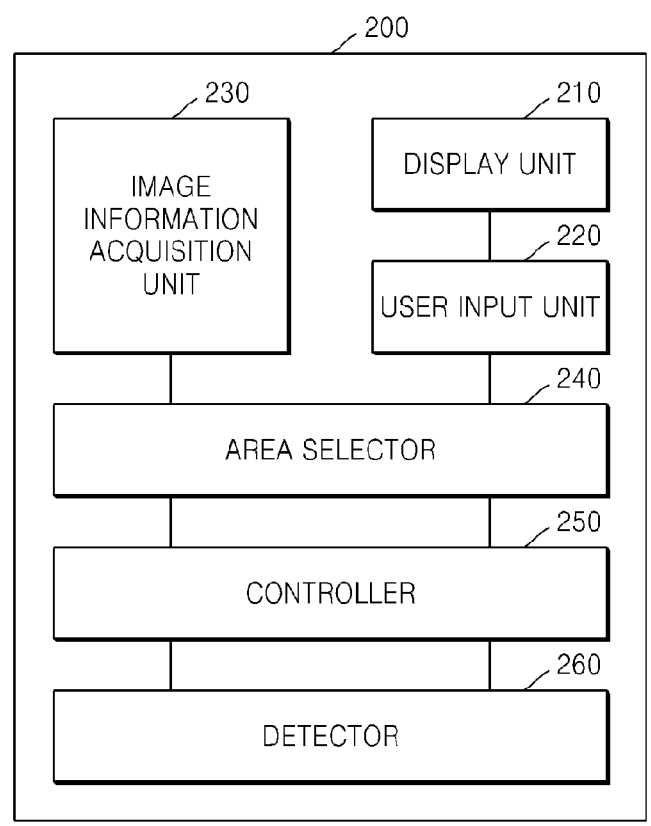
FIG. 5 is a block diagram of an apparatus for adjusting an X-ray emission range, according to the exemplary embodiments of the present invention.

As described herein, exemplary embodiments of the method and apparatus for adjusting an X-ray emission device of the present invention are shown in FIGS. 1-4B, and an exemplary embodiment of components of the X-ray emission device of the present invention for implementing the method and apparatus of FIGS. 1-4B is shown in FIG. 5.

FIG. 5 is a block diagram of an apparatus 200 for adjusting an X-ray emission range, according to the exemplary embodiments of the present invention.

Referring to FIG. 5, the apparatus 200 may include a display unit 210 for displaying an image obtained by capturing X-rays which pass through a subject, a user input unit 220 for receiving a user input with respect to the displayed image, and a controller 250 for controlling a collimator 201, shown in FIGS. 2A-2B and 4A-4B, according to the received user input, such that an X-ray emission range is adjusted according to an aperture size and position of the collimator 201.

In addition, the apparatus 200 may further include an image information acquisition unit 230 for acquiring and processing image information from the image obtained by capturing the X-rays which pass through the subject, and an area selector 240 for selecting a predetermined area 260b, 260c in an image captured based on the user input, as shown in FIGS. 2A-2B and 4A-4B, respectively.

In addition, the apparatus 200 may further include a detector 260 for detecting an emitted X-ray.

The display unit 210 may display an image captured in real time by emitting a continuous or intermittent X-ray. According to the exemplary embodiment of the present invention, the image obtained by capturing X-rays which pass through the subject may include a moving picture. In addition, the image obtained by capturing such X-rays passing through the subject may include an X-ray photograph as the captured image. The display unit 210 may also provide a magnified image of a predetermined area selected by the area selector 240, such as the areas 260b shown in FIGS. 2A-2B, or the area 260c shown in FIGS. 4A-4B. The magnified image that may be provided in addition to the captured image may be magnified using a variable scale, and may be displayed in a pop-up form on the image displayed on the display unit 210 and obtained by capturing the X-rays which pass through the subject, or the magnified image may be displayed on an entire screen of the display unit 210.

The user input unit 220 may receive an input through a user's touch on the display unit 210 on which the captured image is displayed. For example, the user input unit 220 may include an electronic device, such as a touch pad, capable of recognizing the user's touch, for example, by a finger, stylo, or pen used by the user. The user input unit 220 may also include electronic devices, such as a remote control, a mouse, and a joystick, capable of recognizing an input from the user.

The user input unit 220 may also receive an input from the user's voice, and accordingly, the user input unit 220 may include a microphone.

For example, the input by the user's voice may include an input signal generated by the user's voice, and this signal may include a command that causes a device to perform a specific function. The specific function may include, for example, the area selection function for selecting a predetermined area in a captured image.

The user input unit 220 may also receive an input from the user's movement. For example, an input signal, generated based on the user's movement and recognized by a sensor unit (not shown), may be received, and this signal may indicate, for example, a signal including a command that causes a device to perform a specific function. The specific function may include, for example, the area selection function for selecting a predetermined area in a captured image.

The image information acquired by the image information acquisition unit 230 may include information regarding brightness of the captured image. The image information acquisition unit 230 may acquire image information from an image obtained by capturing X-rays passing through a subject into which contrast media are injected.

Figure 2A:
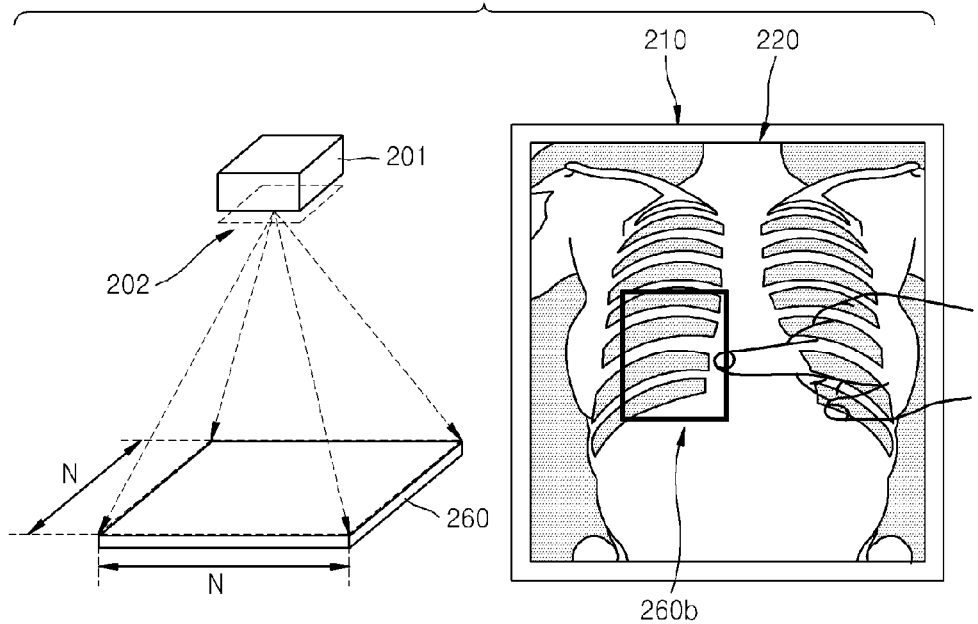
FIG. 2A is a schematic diagram that illustrates X-ray emission in a state where an aperture of a collimator is fully open, according to the exemplary embodiment of the present invention.
Figure 2B:
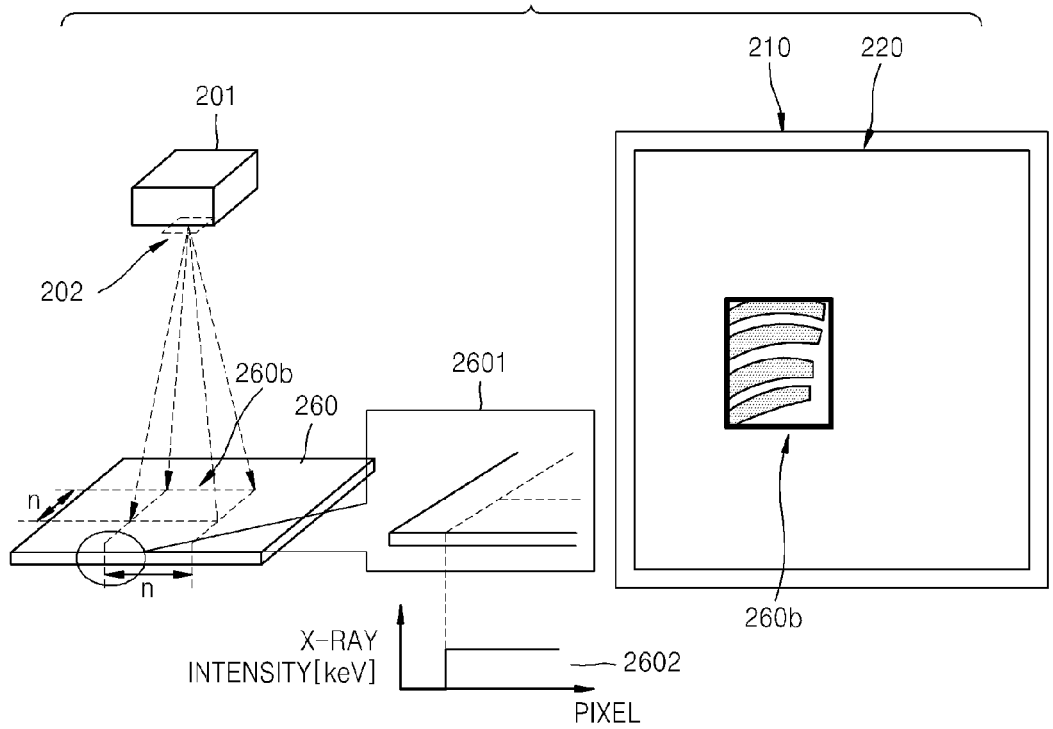
FIG. 2B is a schematic diagram that illustrates controlling of a position or aperture size of the collimator, according to the exemplary embodiment of the present invention.
Figure 2C:
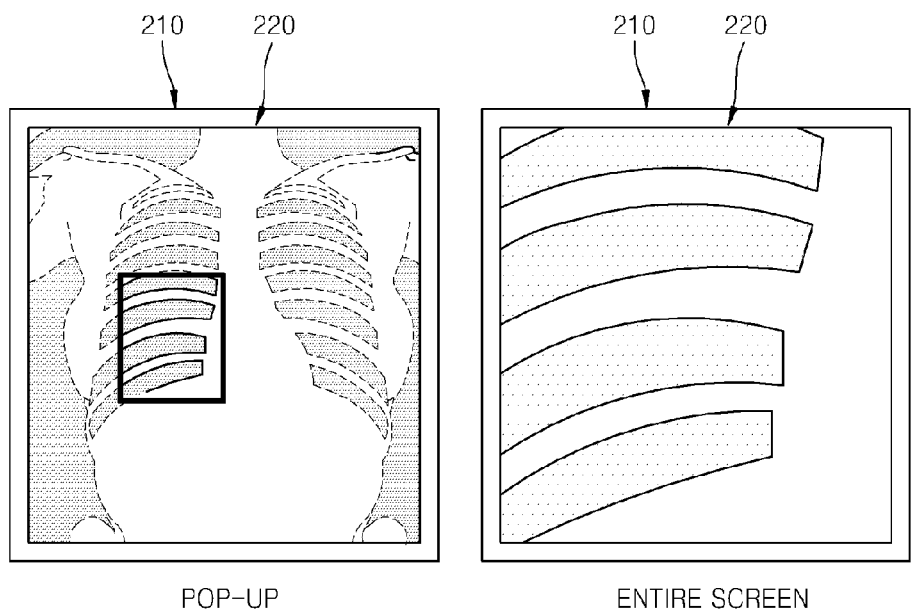
FIG. 2C shows a magnified image in the selected predetermined area in which the magnified image may be magnified using a variable scale displayed in a pop-up form on the image obtained by capturing the X-rays passing through the subject, or displayed on an entire screen of the display according to the exemplary embodiment of the present invention.

The area selector 240 may select the predetermined area 260b in the captured image, such as shown in FIGS. 2A-2B, based on the user input received by the user input unit 220. The predetermined area 260b may be selected in a form defined by a boundary of the predetermined area 260b generated by moving a cursor movable on the display unit 210 or selected in a pre-set form. The pre-set form may include, for example, a polygon, a circle, or any other shape.

In addition, referring to FIGS. 4A-4B, the area selector 240 may detect at least one point 410, 420 satisfying a predetermined criterion from the captured image based on the information regarding the brightness of the captured image. In addition, the area selector 240 may select the predetermined area 260c in the captured image based on the detected at least one point 410, 420. The predetermined criterion may include, for example, a criterion that a brightness change ratio of a captured image is maximized. The predetermined area 260c may be selected in a pre-set form to include at least one point. The pre-set form may include, for example, a polygon, a circle, or any other shape.

The controller 250 may adjust a size of an aperture 202 of the collimator 201 based on the selected predetermined areas 260b or 260c, as in FIGS. 2A-2B and FIGS. 4A-4B, respectively. For example, the controller 250 may adjust the aperture size of the collimator 201 so that a ratio of an area of the selected predetermined area 260b or 260c to a total area of the image obtained by capturing the X-rays passing through the subject corresponds to a ratio of the aperture size of the collimator 201b in a partially open state to the aperture size of the collimator 201 in a fully open state.

In addition, the controller 250 may adjust a position of the collimator 201 based on a location of the selected predetermined area 260b or 260c selected by the area selector 240. For example, the position of the collimator 201 may be adjusted to include pixels of the detector 260 corresponding to the location of the selected predetermined area 260b or 260c. The adjusting of the position of the collimator 201 may include adjusting an emission angle of an X-ray or a radioactive ray emitted from the collimator 201.

In addition, the apparatus 200 may further include the detector 260 for detecting an emitted X-ray. The detector 260 may detect the intensity of the X-rays with respect to an image captured using the X-rays emitted from the collimator 201.

FIG. 1 is a flowchart illustrating a method of adjusting an X-ray emission range, according to the exemplary embodiment of the present invention.

Referring to FIG. 1, the method may include displaying an image obtained by capturing X-rays passing through a subject in step 110, receiving a user input with respect to the captured image in step 120, and controlling the collimator 201 according to the received user input in step 130. In the method, an X-ray emission range may be adjusted according to the aperture size and position of the collimator.

Referring to FIGS. 2A-2B, in the exemplary embodiment of the present invention, the step 110 of displaying the image is performed using the display unit 210, the step 120 of receiving the user input is performed by a user using the user input unit 220, and the step 130 of controlling the collimator 201 is performed by the controller 250 sending control signals to the collimator 201.

In the displaying of the image obtained by capturing the X-rays passing through the subject in step 110, an image captured in real time by continuously or intermittently emitting an X-ray onto the subject may be displayed. In addition, the image may include a moving picture. In addition, the image may include an X-ray photograph.

The receiving of the user input with respect to the captured image in step 120 may include receiving the user input for selecting a predetermined area in the captured image. The user input for selecting the predetermined area may include an input through a user's touch to the display unit 210 on which the captured image is displayed, as in FIGS. 2A-2B. In such an exemplary embodiment, the display unit 210 and the user input unit 220 may be implemented using a touch screen which displays images; which responds to user touches with a user's finger, stylo, or other devices; and which generates corresponding input signals to be processed. For example, the user may directly touch the display unit 210 to select the predetermined area in the captured image, such as the areas 260b in FIGS. 2A-2B. The predetermined area may be selected in a form defined by a boundary of the predetermined area generated by moving a cursor (not shown) movable on the display unit 210 or selected in a pre-set form. The pre-set form may include, for example, a polygon, a circle, or other known shapes. Accordingly, the area 260b may be generated by the user moving his/her finger or stylo on the display 210 to generate the shape of the predetermined area 260b using known graphic user interface (GUI) methods, such as methods for specifying and/or delimiting the area 260b on the touch screen of the display unit 210 and user input unit 220 of FIGS. 2A-2B.

In addition, the receiving of the user input with respect to the captured image in step 120 may include receiving an input of an audible sound, for example, the user's voice. In an exemplary embodiment, the user input unit 220 shown in FIG. 5 may include a microphone to receive and process the audible sound such as the user's voice.

For example, the input by the user's voice may include an input signal generated by the user's voice, and this signal may indicate, for example, a signal including a command that causes a device to perform a specific function. The specific function may include, for example, an area selection function, which is performed by the area selector 240 shown in FIG. 5, for selecting a predetermined area in a captured image.

The receiving of the user input with respect to the captured image in step 120 may also include receiving an input by the user's movement. For example, an input signal generated based on the user's movement recognized by a sensor unit (not shown) may be received, and this signal may indicate, for example, a signal including a command that causes a device to perform a specific function. The specific function may include, for example, the area selection function for selecting a predetermined area in a captured image. In an alternative embodiment, the user input unit 220, shown in FIG. 5, may include the sensor unit described herein.

The controlling of the collimator 201 according to the received user input in step 130 may include adjusting an aperture size of the collimator 201 based on the selected predetermined area. The adjusting of the aperture size of the collimator 201 based on the selected predetermined area may include, for example, adjusting the aperture size of the collimator 201 so that a ratio of an area of the selected predetermined area to a total area of the image obtained by capturing the X-rays passing through subject corresponds to a ratio of the aperture size of the collimator 201 in a partially open state to the aperture size of the collimator 201 in a fully open state. For example, the collimator 201 may include an aperture 202 which has a fully open state as shown in FIG. 2A, and a partially open state as shown in FIG. 2B. The size of the aperture 202 is controlled using control signals from the controller 250 in FIG. 5 which are generated in response to the received user input through the user input unit 220.

In addition, the controlling of the collimator 201 according to the received user input in step 130 may include adjusting a position of the collimator 201 based on a location of the selected predetermined area 260b, 260c in the image obtained by capturing X-rays passing through the subject. For example, the position of the collimator 201 may be adjusted to include pixels of a detector 260 corresponding to the location of the selected predetermined area 260b. The adjusting of the position of the collimator 201 may include adjusting an emission angle of an X-ray or a radioactive ray emitted from the collimator 201. For example, the controller 250 may generate control signals which control the collimator 201 to move in relation to the detector 260 and/or to adjust the emission angle using at least one motor attached to or included in the collimator 201.

In addition, the method may further include detecting the emitted X-ray. For example, the method may further include detecting the intensity of the X-ray with respect to an image captured using the X-ray emitted from the collimator 201 in step 140. The detecting in step 140 is performed by a detector 260, shown in the exemplary embodiments in FIGS. 2A-2B and 5.

The method may further include providing a magnified image in the selected predetermined area 260b, in which the magnified image that may be magnified using a variable scale is displayed in a pop-up (see FIG. 2C) form on the image obtained by capturing the X-rays passing through the subject or displayed on an entire screen of the display unit 210.

FIG. 2A is a schematic diagram that illustrates X-ray emission in a state where a collimator 201 is fully open, for example, with the aperture 202 fully open, and FIG. 2B is a schematic diagram that illustrates controlling of a position of the collimator 201 or the size of the aperture 202 of a collimator 201b, according to the exemplary embodiment of the present invention.

As shown in FIG. 2A, an X-ray may be emitted in a state where the collimator 201 is fully open by fully opening the aperture 202, for example, in response to control signals from the controller 202, and an image obtained by capturing X-rays passing through a subject may be acquired through a display unit 210 based on an X-ray detected by the entire pixels of a detector 260. It will be understood that the subject, not shown in FIG. 2A, is positioned between the collimator 201 and the detector 260, with the X-rays from the collimator 201 passing through the subject before reaching the detector 260.

According to another embodiment of the present invention, the image may include a moving picture. In addition, the image may include an X-ray photograph.

For example, assuming that a time taken to detect an X-ray per pixel in a detector having N×N pixels (N is a positive integer) is T seconds, a total of N×N×T seconds may be required to detect an X-ray by the entire set of pixels in the detector 260 having N×N pixels.

According to the exemplary embodiment of the present invention, by adjusting a size of the aperture 202 or position of the collimator 201, an X-ray emission range may be adjusted, as shown in FIG. 2B with the collimator 201b having a smaller aperture 202 and/or a different position relative to the detector 260. For example, an X-ray emitted from the collimator 201b obtained by adjusting the aperture size or position of the collimator 201 in FIG. 2A, to be configured as the collimator 201b in FIG. 2B, based on a user input received by a user input unit 220, such as a touch pad, may be detected in a predetermined area 260b of the detector 260, as shown in FIG. 2B. Assuming that the predetermined area 260b has n×n pixels (n is a positive integer, n<N) and a time taken to detect an X-ray per pixel in the detector 260 is T seconds, a time required to detect an X-ray emitted to the predetermined area 260b of the detector 260 may be n×n×T seconds. For example, referring to inset 2601 of FIG. 2B, by detecting the X-ray intensity in the predetermined area 260b of the detector 260, as shown by a graph 2602, without detecting an X-ray intensity in all the pixels of the detector 260, an X-ray detection time required by the detector 260 to obtain an image of a specific diagnosis area of the subject, such as a patient, may be reduced. It will be understood that the subject, not shown in FIG. 2B, is positioned between the collimator 201b and the detector 260, with the X-rays from the collimator 201b passing through the subject before reaching the detector 260.

Thus, if an aperture size or position of the collimator 201 is adjusted from the configuration shown in FIG. 2A to the configuration shown in FIG. 2B, a time taken to detect an X-ray emitted to the detector 260 by the collimator 201b in FIG. 2B may be reduced compared to when an X-ray is emitted by the collimator 201 is in a fully open state as in FIG. 2A, and the number of pixels to which the X-ray is emitted may also be reduced, thereby reducing an amount of data to be processed to generate a digital image. Accordingly, instead of X-ray photographing the entire subject, an X-ray technician or doctor may focus the X-ray photographing procedure on a specific diagnosis area of interest of the subject, such as a suspected location of a tumor, thus decreasing the image processing time for the X-ray photographing procedure.

FIG. 3 is a flowchart illustrating a method of adjusting an X-ray emission range, according to an alternative exemplary embodiment of the present invention, and FIGS. 4A-4B are schematic diagrams illustrating controlling of a position or aperture size of the collimator 201, according to the alternative embodiment of the present invention. The method will now be described in more detail with reference to FIGS. 3 and 4A-4B.

Referring to FIGS. 3 and 4A-4B in conjunction with FIG. 5, the method may include acquiring image information from an image obtained by capturing X-rays passing through a subject in step 310, selecting a predetermined area 260c in the captured image based on the acquired image information in step 320, and controlling the collimator 201 based on the selected predetermined area in step 330, in which an X-ray emission range is adjusted according to an aperture size and position of the collimator 201 initially in the configuration shown in FIG. 4A to be in the configuration of the collimator 201b shown in FIG. 4B. In addition, the method may further include detecting an emitted X-ray in step 340, in which the detecting of the emitted X-ray in step 340 may include detecting the intensity of the X-ray with respect to an image captured by the detector 260 using the X-ray emitted from the collimator 201b. It will be understood that the subject, not shown in FIGS. 4A-4B, is positioned between the collimator 201, 201b, respectively, and the detector 260, with the X-rays from the collimator 201, 201b passing through the subject before reaching the detector 260.

The image may include a moving picture. In addition, the image may include an X-ray photograph.

The method may further include injecting contrast media into the subject. In addition, in the method, image information may be acquired from an image obtained by capturing the X-rays passing through the subject by using the contrast media injected into the subject.

In step 310 in which image information is acquired from an image obtained by capturing X-rays passing through a subject, the image information may include information regarding brightness of the captured image.

Step 320, in which a predetermined area 260c in the captured image is selected based on the acquired image information, may include detecting at least one point 410, 420, as shown in FIG. 4A, satisfying a predetermined criterion from the captured image based on the information regarding brightness, and selecting the predetermined area 260c in the captured image based on the points 410, 420 which may define or delimit the predetermined area 260c.

The predetermined criterion may include, for example, a criterion that a brightness change ratio of a captured image is maximized. For example, the image information acquisition unit 230 may calculate a sum of the brightness change ratios of each pixel in the image relative to all of the neighbor pixels of each pixel, and may select points in the image, for example, points 410, 420, such that the calculated sum is maximized, using image processing methods known in the art. The detecting of the at least one point 410, 420 may include detecting the points 410 and 420 at which a pixel brightness change between neighboring pixels is sharp, using the image information acquisition unit 230 shown in FIG. 5. For example, a predetermined threshold, such as 50%, may be used to measure the sharpness of a brightness change. Accordingly, if a pixel at point 410 or 420 has a brightness of at least 50% less than the brightness of its neighboring pixels, due to greater absorption of X-rays, than the pixel at point 410 or 420 is selected for inclusion in the predetermined area 260c.

The contrast media include materials known in the art for clearly viewing a brightness change of an image by artificially increasing an X-ray absorption difference between tissues to more clearly observe a tissue or a blood vessel with the contrast media injected into, for example, a stomach, an intestinal canal, or a blood vessel in an X-ray or a radiation examination. That is, a boundary of a tissue may be clearly distinguished from surrounding tissues by making a brightness change of an image vivid by using contrast media capable of transmitting or absorbing an X-ray better compared with the surrounding tissues. For example, when an X-ray image of a tissue of a subject is captured by using contrast media absorbing an X-ray better than surrounding tissues, the tissue in which the contrast media is absorbed may be viewed to be darker than the surrounding tissues of the subject. That is, when the contrast media is used, points at which a brightness change between pixels is sharp may be easily detected.

In addition, the method may include selecting the predetermined area 260c in the captured image based on the detected at least one point 410, 420. For example, the predetermined area 260c may be selected in a form pre-set to include the detected at least one point 410, 420. The pre-set form may include, for example, a polygon, a circle, or any other shape.

Step 330 of FIG. 4, in which the collimator 201 is controlled based on the selected predetermined area 260c, may include, for example, adjusting a size of the aperture 202 of the collimator 201 so that a ratio of an area of the selected predetermined area 260c to a total area 260 of the image obtained by capturing the X-rays passing through the subject corresponds to a ratio of a size of the aperture 202 of the collimator 201b in a partially open state to a size of the aperture 202 of the collimator 201 in a fully open state, as shown in FIGS. 4B and 4A, respectively.

Alternatively, step 330, in which the collimator 201 is controlled based on the selected predetermined area 260c, may include adjusting a position of the collimator 201 based on a location of the selected predetermined area 260c in the image obtained by capturing the X-rays passing through the subject. For example, the position of the collimator 201 may be adjusted from the position of the collimator 201 in FIG. 4A to the position of the collimator 201b in FIG. 4B which places the collimator 201b closer to the detector 260, to include pixels of the detector 260 corresponding to the location of the selected predetermined area 260c. Alternatively or in addition to moving the collimator 201b closer to the detector 260, the adjusting of the position of the collimator 201 may include adjusting an emission angle of the X-rays emitted from the collimator 201. For example, the controller 250 may generate control signals which control the collimator 201 to move in relation to the detector 260 and/or to adjust the emission angle using at least one motor attached to or included in the collimator 201.

In addition, the method may further include detecting an emitted X-ray in step 340, and the detecting of the emitted X-ray in step 340 may include detecting the intensity of the X-ray with respect to an image captured using the X-ray emitted from the collimator 201.

Referring to FIGS. 3 and 4A-4B again, a subject may be captured in a fully open state of the aperture 202 of the collimator 201, shown in FIG. 4A. To more finely observe a subject to be captured, contrast media absorbing an X-ray, for example, may be used. Image information including information regarding brightness of an image of a subject captured by using contrast media may be acquired from the image in step 310. For example, the image information includes brightness information and identifying information, such as coordinates of the points 410 and 420 at which a brightness change is sharp. The information regarding brightness may include a location of a pixel of the detector 260 and an image brightness value of the pixel. The predetermined area 260c in the captured image may be selected based on the acquired image information in step 320. An aperture size or position of the collimator 201 may be adjusted from an initial position of the collimator 201, shown in FIG. 4A, to a different position of the collimator 201b shown in FIG. 4B, based on the selected predetermined area 260c in step 330. The intensity of an X-ray emitted through the adjusted collimator 201 may be detected in step 340.

The above-described apparatus and methods according to the present invention can be implemented in hardware, firmware or as software or computer code that can be stored in a recording medium such as a CD ROM, a RAM, a ROM, a floppy disk, DVDs, a hard disk, a magnetic storage media, an optical recording media, or a magneto-optical disk or computer code downloaded over a network originally stored on a remote recording medium, a computer readable recording medium, or a non-transitory machine readable medium and to be stored on a local recording medium, so that the methods described herein can be rendered in such software that is stored on the recording medium using a general purpose computer, a digital computer, or a special processor or in programmable or dedicated hardware, such as an ASIC or FPGA. As would be understood in the art, the computer, the processor, microprocessor controller or the programmable hardware include memory components, e.g., RAM, ROM, Flash, etc. that may store or receive software or computer code that when accessed and executed by the computer, processor or hardware implement the processing methods described herein. In addition, it would be recognized that when a general purpose computer accesses code for implementing the processing shown herein, the execution of the code transforms the general purpose computer into a special purpose computer for executing the processing shown herein.

While the present invention has been particularly shown and described with reference to exemplary embodiments thereof, it will be understood by those of ordinary skill in the art that various changes in form and details may be made therein without departing from the spirit and scope of the present invention as defined by the following claims. The exemplary embodiments should be considered in descriptive sense only and not for purposes of limitation. Therefore, the scope of the present invention is defined not by the detailed description of the present invention but by the appended claims, and all differences within the scope will be construed as being included in the present invention.

What is claimed is:

1. A method of adjusting an X-ray emission range, the method comprising:
    displaying an image obtained by capturing X-rays passing through an object;
    receiving an input for selecting an area in the captured image;
    adjusting at least one of an aperture size or a position of a collimator so that the X-ray emission range corresponds to the selected area; and providing a magnified image of the selected area, wherein the magnified image is magnified at a variable scale and is displayed in a pop-up form on the image obtained by capturing the X-rays passing through the object, or displayed on an entire screen.

2. The method of claim 1, wherein the image is a moving picture.

3. The method of claim 1, wherein the image is an X-ray photograph.

4. The method of claim 1, wherein the aperture size of the collimator is adjusted based on the selected area.

5. The method of claim 1, wherein the position of the collimator is adjusted based on a location of the selected area in the captured image.

6. The method of claim 1, wherein the receiving of the input for selecting the area comprises receiving an input through a touch on a display unit on which the captured image is displayed.

7. The method of claim 1, wherein the receiving of the input for selecting the area comprises receiving an input of an audible sound.

8. The method of claim 1, wherein the receiving of the input for selecting the area comprises receiving an input of a selected movement.

9. The method of claim 1, further comprising detecting emitted X-rays, wherein the detecting of the emitted X-rays comprises detecting an intensity of the X-rays with respect to just the selected area of the captured image using the X-rays emitted from the adjusted aperture size or position of the collimator.

10. A computer-readable recording medium storing a computer-readable program for executing the method of claim 1.

11. A method of adjusting an X-ray emission range, the method comprising:
    acquiring an image obtained by capturing X-rays passing through an object;
    selecting an area in the image based on a brightness of the image; and
    adjusting at least one of an aperture size or a position of a collimator so that the X-ray emission range corresponds to the selected area.

12. The method of claim 11, wherein the image is a moving picture.

13. The method of claim 11, wherein the image is an X-ray photograph.

14. The method of claim 1, further comprising injecting contrast media into the object, wherein the image is obtained by capturing the X-rays passing through the object having the contrast media therein.

15. The method of claim 1, wherein the selecting of the area comprises:
    detecting at least one point satisfying a predetermined criterion from the image based on the brightness of the image; and
    selecting the area in the image based on the detected at least one point.

16. The method of claim 15, wherein the predetermined criterion is a criterion that a brightness change ratio of the image is maximized.

17. The method of claim 1, wherein the aperture size of the collimator is adjusted based on the selected area.

18. The method of claim 1, wherein the position of the collimator is adjusted based on a location of the selected area in the image.

19. The method of claim 1, further comprising detecting emitted X-rays,
    wherein the detecting of the emitted X-rays comprises detecting the intensity of the X-rays with respect to just the selected area of the image using the X-rays emitted from the collimator.

20. An apparatus for adjusting an X-ray emission range, the apparatus comprising:
    a display unit for displaying an image obtained by capturing X-rays passing through an object;
    an input unit for receiving an input for selecting an area in the displayed image; and
    a controller for adjusting at least one of an aperture size or a position of a collimator so that the X-ray emission range corresponds to the selected area,
    wherein the display unit additionally provides a magnified image of the selected area, and the magnified image that is magnified at a variable scale and is displayed in a pop-up form on the image obtained by capturing the X-rays passing through the object, or displayed on an entire screen.

21. The apparatus of claim 20, wherein the image is a moving picture.

22. The apparatus of claim 20, wherein the image is an X-ray photograph.

23. The apparatus of claim 20, wherein the controller adjusts the aperture size of the collimator based on the selected area.

24. The apparatus of claim 20, wherein the controller adjusts the position of the collimator based on a location of the selected area in the displayed image.

25. The apparatus of claim 20, wherein the input unit receives the input through a touch on the display unit on which the captured image is displayed.

26. The apparatus of claim 20, wherein the input unit receives the input of an audible sound.

27. The apparatus of claim 20, wherein the input unit receives the input of a selected movement.

28. The apparatus of claim 20, further comprising a detector for detecting emitted X-rays,
    wherein the detector detects the intensity of the X-rays with respect to just the selected area of the image using the X-rays emitted from the collimator.

29. An apparatus for adjusting an X-ray emission range, the apparatus comprising:
    an image information acquisition unit for acquiring an image obtained by capturing X-rays passing through an object;

an area selector for selecting an area in the image based on a brightness of the image; and a controller for adjusting at least one of an aperture size or a position of a collimator so that the X-ray emission range corresponds to the selected area.

30. The apparatus of claim 29, wherein the image is a moving picture.

31. The apparatus of claim 29, wherein the image is an X-ray photograph.

32. The apparatus of claim 29, wherein the image information acquisition unit acquires the image obtained by capturing the X-rays passing through the object into which contrast media are injected.

33. The apparatus of claim 29, wherein the area selector detects at least one point satisfying a predetermined criterion from the captured image based on the brightness of the image and selects the area in the image based on the detected at least one point.

34. The apparatus of claim 33, wherein the predetermined criterion is a criterion that a brightness change ratio of the image is maximized.

35. The apparatus of claim 29, wherein the controller adjusts the aperture size of the collimator based on the selected area.

36. The apparatus of claim 29, wherein the controller adjusts the position of the collimator based on a location of the selected area in the captured image.

37. The apparatus of claim 29, further comprising a detector for detecting emitted X-rays, wherein the detector detects the intensity of the X-rays with respect to just the selected area of the image using the X-rays emitted from the collimator.

* * * * *

UNITED STATES PATENT AND TRADEMARK OFFICE
CERTIFICATE OF CORRECTION

| | | |
|---|---|---|
| PATENT NO. | : 9,271,687 B2 | Page 1 of 1 |
| APPLICATION NO. | : 13/551719 | |
| DATED | : March 1, 2016 | |
| INVENTOR(S) | : Byoung-hoon Koh | |

It is certified that error appears in the above-identified patent and that said Letters Patent is hereby corrected as shown below:

Column 11, Claim 14, Line 66 should read as follows:
--...claim 11, further comprising...--

Column 12, Claim 15, Line 4 should read as follows:
--...claim 11, wherein the...--

Column 12, Claim 17, Line 14 should read as follows:
--...claim 11, wherein the...--

Column 12, Claim 18, Line 16 should read as follows:
--...claim 11, wherein the...--

Column 12, Claim 19, Line 19 should read as follows:
--...claim 11, further comprising...--

Column 12, Claim 20, Line 36 should read as follows:
--...scale is displayed in...--

Signed and Sealed this
Third Day of May, 2016

Michelle K. Lee
*Director of the United States Patent and Trademark Office*